US 6,637,430 B1

(12) United States Patent
Voges et al.

(10) Patent No.: US 6,637,430 B1
(45) Date of Patent: Oct. 28, 2003

(54) RESPIRATORY DELIVERY SYSTEM WITH POWER/MEDICAMENT RECHARGE ASSEMBLY

(75) Inventors: Robert M. Voges, Solana Beach, CA (US); Wolfgang H. Hanisch, Indooroopilly (AU); Olaf Reinhold, San Diego, CA (US)

(73) Assignee: Ponwell Enterprises Limited, Wan Chai (CN)

( * ) Notice: Subject to any disclaimer, the term of this patent is extended or adjusted under 35 U.S.C. 154(b) by 139 days.

(21) Appl. No.: 09/595,722

(22) Filed: Jun. 16, 2000

(51) Int. Cl.⁷ .............................. A61M 11/00; B65B 1/04
(52) U.S. Cl. ........................... 128/200.14; 128/200.16; 128/202.21; 128/203.21; 141/2; 141/329; 141/330
(58) Field of Search ................... 128/200.14, 200.19, 128/200.23, 203.15, 202.21, 203.21, 200.16; 239/338; 222/165, 82, 135; 141/329, 330, 351, 19, 2; 131/194, 195

(56) References Cited

U.S. PATENT DOCUMENTS

| 2,603,215 A | | 7/1952 | Arnow ........................ 128/206 |
| 3,661,189 A | * | 5/1972 | Bowser et al. ................. 141/1 |
| 3,831,606 A | | 8/1974 | Damani ....................... 128/266 |
| 3,971,377 A | | 7/1976 | Damani ....................... 128/266 |
| 4,147,166 A | | 4/1979 | Hansen ........................ 128/266 |
| 4,877,065 A | * | 10/1989 | Lamboy et al. ............. 141/113 |
| 5,186,164 A | | 2/1993 | Raghuprasad .......... 128/200.14 |
| 5,327,883 A | | 7/1994 | Williams et al. ........ 128/203.12 |
| 5,492,112 A | | 2/1996 | Mecikalski et al. ..... 128/203.15 |
| 5,505,236 A | * | 4/1996 | Grabenkort et al. ... 128/202.27 |
| 5,551,416 A | * | 9/1996 | Stimpson et al. ...... 128/200.16 |
| 5,583,831 A | | 12/1996 | Churchill et al. ............. 368/10 |
| 5,642,727 A | | 7/1997 | Datta et al. ............. 128/203.15 |
| 5,881,716 A | | 3/1999 | Wirch et al. ........... 128/200.16 |
| 5,961,011 A | * | 10/1999 | Thomas et al. ............. 141/329 |
| 6,129,125 A | * | 10/2000 | Duchon et al. ............... 141/18 |
| 6,321,798 B1 | * | 11/2001 | Solignac ..................... 141/192 |

FOREIGN PATENT DOCUMENTS

WO    WO 97/18846    5/1997

* cited by examiner

Primary Examiner—Weilun Lo
Assistant Examiner—Mital Patel
(74) Attorney, Agent, or Firm—Marsh Fischmann & Breyfogle LLP

(57) ABSTRACT

A respiratory delivery system is disclosed which preferably includes both medicament and plower recharge capabilities. The system includes a portable inhaler with a rechargeable medicament cartridge and a rechargeable power supply. This power supply may be electrically interconnected with one or more components of the portable inhaler, including a droplet ejection device, a controller for the droplet ejection device, an actuation switch, an inhalation sensor, and/or an electronic memory. The system further includes a recharging unit which includes an inhaler docking station, a medicament recharging system, and a power recharging system. When the portable inhaler is docked to the recharging unit, the recharging unit recharges the power supply of the portable inhaler and recharges the medicament cartridge of the portable inhaler by providing additional medicament thereto.

47 Claims, 4 Drawing Sheets

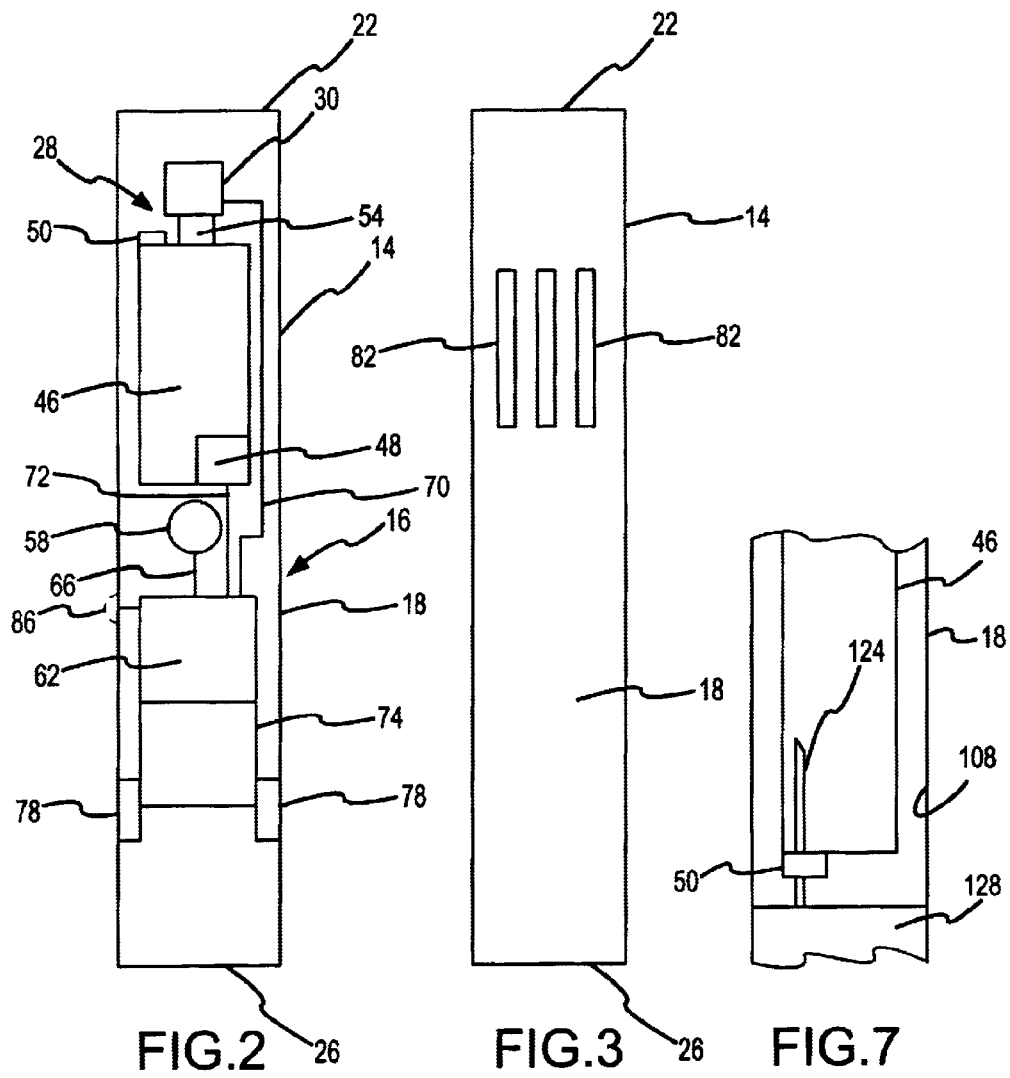
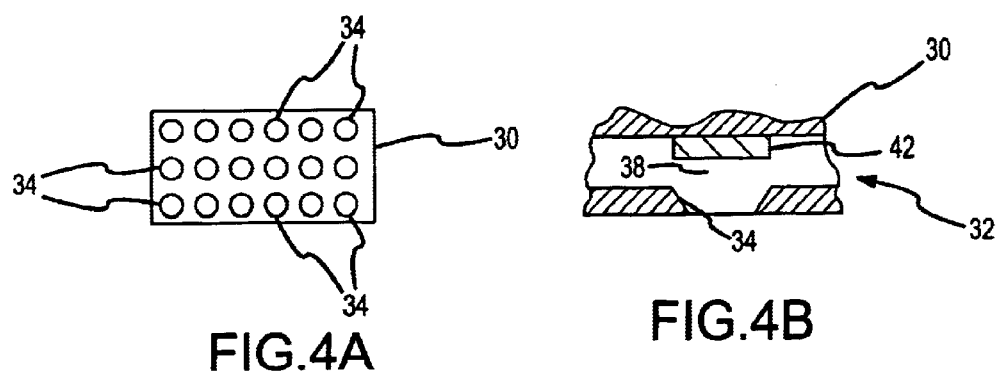
FIG.2  FIG.3  FIG.7
FIG.4A  FIG.4B

RESPIRATORY DELIVERY SYSTEM WITH POWER/MEDICAMENT RECHARGE ASSEMBLY

CROSS-REFERENCE TO RELATED APPLICATIONS

Not applicable.

STATEMENTS REGARDING FEDERALLY SPONSORED RESEARCH OR DEVELOPMENT

Not applicable.

FIELD OF THE INVENTION

The present invention generally relates to the field of respiratory or inhalation therapy and, more particularly, to a respiratory delivery system which includes a portable inhaler and a recharging unit which may be used to recharge both the power and medicament supply of the portable inhaler.

BACKGROUND OF THE INVENTION

Many types of medicaments are delivered by inhalation for treating/addressing various types of conditions. Three general types of inhalers may be used for this type of "respiratory therapy." Metered dose inhalers ("MDIs") are relatively small, portable units which have a medicament disposed within a container of a pressurized gas or propellant (e.g. mixture of medicament and propellant). The patient typically pushes down on this container to direct a "burst" of a mixture of propellant and medicament into the patient's mouth during an inhalation, the propelling "burst" being provided by the pressure within the container. A fixed number of doses are available in a given MDI. When all of the medicament has been dispensed from the container, typically the MDI or at least the container of medicament/propellant is discarded.

Another categorical type of inhaler is a nebulizer. These types of inhalers are not as portable as an MDI, and are more commonly used in a clinic or hospital setting. Generally, a nebulizer houses an appropriate medicament in liquid form. Gas from an external source is directed through an appropriate line under pressure and into the nebulizer to aerosolize the medicament for transport to,the patient for delivery by inhalation. At the end of the treatment or upon the consumption of all of the liquid medicament in the nebulizer, and typically after a sterilization procedure, additional liquid medicament may be poured into the nebulizer for subsequent treatments.

The third general type of inhaler has a degree of portability which is similar to that of the MDI, but which uses sources other than an external supply of pressurized gas to generate droplets of the desired medicament. Some inhalers of this type use a small "on-board" source of pressurized gas to aerosolize a liquid medicament. Other inhalers use piezoelectric crystals and the like to aerosolize a liquid medicament in some manner. U.S. Pat. No. 5,894,841 to Voges, entitled "Dispenser," discloses another inhaler of this general categorical type, but which uses a "droplet on demand" ejection device to generate droplets of medicament in a desired manner (e.g., a piezoelectric device of the kind used in ink jet printing or a thermal "bubble jet" device of the kind used in inkjet printing). The cartridge of medicament in the inhaler from U.S. Pat. No. 5,894,841 may be replaced after its medicament has been consumed or spent.

What are more typically viewed as non-medical devices have also been available for some time to deliver nicotine. Typically these devices at least attempt to simulate the appearance of a cigarette and provide a certain amount of nicotine. Known devices of this type are either designed to be disposable or to allow replacement of the nicotine cartridges/containers used thereby.

BRIEF SUMMARY OF THE INVENTION

The present invention is embodied in a respiratory delivery system which has "recharge" capabilities. In this regard, the subject respiratory delivery system generally includes typically one or more portable inhalers and a recharging unit. Having multiple portable inhalers allows one portable inhaler to be undergoing a recharge via the recharging unit while at least one other portable inhaler is available for use. Components of the portable inhaler include an inhaler housing, a container with an appropriate flowable substance disposed therein (e.g., a medicament in liquid and/or powder in a suspension), and an inhaler outlet of some sort. Flowable substance from the container is directed through the inhaler outlet for discharge into the mouth or nose of an individual who is using the portable inhaler. The inhaler outlet need not be in constant fluid communication with the flowable substance container. Typically the inhaler outlet will be in the form of some type of a mouthpiece or the like for oral delivery, or a nose piece for nasal delivery, of the flowable substance from the portable inhaler to the individual which is using the portable inhaler (e.g., in the form of the "tip" of a cigarette).

The recharging unit includes an inhaler docking station and a flowable substance recharging system. The flowable substance recharging system of the recharging unit includes a flowable substance recharging reservoir and a flowable substance recharging fixture which interfaces with the flowable substance container of the portable inhaler when the portable inhaler is disposed at the docking station of the recharging unit. Flowable substance from the flowable substance recharging system thereby may be directed from the flowable substance recharging reservoir of the recharging unit, through the flowable substance recharging fixture of the recharging unit, and into the flowable substance container of the portable inhaler when the portable inhaler is "docked" at the recharging unit.

Various refinements exist of the features noted in relation to the present invention. Further features may also be incorporated in the present invention as well. These refinements and additional features may exist individually or in any combination. With regard to the portable inhaler, its inhaler housing may be configured to a least generally approximate a configuration and size of a cigarette. Another way of characterizing the inhaler housing is as a cylinder having a length of approximately 85 mm and a diameter of approximately 10 mm.

The inhaler housing may include at least one inhaler inlet through which air may be drawn into the inhaler housing. One way of characterizing this inhaler inlet(s) is relative to the position of the inhaler outlet of the portable inhaler. Consider the case where the inhaler housing has first and second ends (e.g., the above-noted cylindrical configuration). The inhaler outlet may be disposed at and/or define the second end of the inhaler housing, and each inhaler inlet may be disposed closer to the second end of the inhaler housing than its first end. In one embodiment, the first end of the inhaler housing, or that end of the inhaler housing which is opposite that which includes the inhaler outlet, may be closed. Therefore, the inhaler inlet(s) may be disposed on a sidewall of the inhaler housing of sorts versus on one of its ends.

A plurality of inhaler inlets may be utilized for the portable inhaler, and these inhaler inlets may be disposed about the inhaler housing in at least substantially equally, radially spaced relation. Consider the case where the inhaler housing is in the form of a cylinder as noted above. Each adjacent pair of inhaler inlets may be separated by an equal angular spacing which would be measured relative to a central, longitudinal axis about which this cylinder is formed. The noted plurality of inhaler inlets may also take the form of air intake slots. Each of these air intake slots may have a longitudinal extent which is at least generally parallel with a longitudinal extent of the inhaler housing.

The flowable substance container of the portable inhaler may be sized so as to hold no more than about 50 doses. A "dose" for purposes of the present invention is an amount of the flowable substance which is provided to an individual using the portable inhaler during one inhalation. This emphasizes the desirability of having flowable substance recharging capabilities for the respiratory delivery system via the recharging unit. In this regard, the flowable substance recharging reservoir of the recharging unit may be sized to hold multiple refill doses of the flowable substance in accordance with the definition presented above (e.g., so as to be available for "refilling" the portable inhaler(s) on multiple occasions; in one embodiment within a range of about 150 doses to about 3,000 doses in accordance with the above definition).

The portable inhaler may include a droplet ejection device which is fluidly interconnected with the flowable substance container for dispensing the flowable substance in the form of a plurality of droplets to an individual which is using the portable inhaler. This droplet ejection device may include a plurality of actuators and a plurality of discharge orifices, with each discharge orifice having its own actuator. Droplet ejection devices of this type for inhaler applications are disclosed in U.S. Pat. No. 5,894,841 to Voges, which issued Apr. 20, 1999, and the entire disclosure of which is incorporated by reference herein. In one embodiment, the droplet ejection device may be characterized as including at least one discharge orifice and at least one actuator, and in yet another embodiment may be characterized as having at least one actuator, with each such actuator having at least one discharge orifice associated therewith. Other types of droplet ejection devices or ways of generating droplets could be utilized by the portable inhaler in relation to the present invention, including a single piezoelectric structure which, when activated, would simultaneously discharge a plurality of droplets through a plurality of discharge orifices or the like (e.g., a solid diaphragm/plate with a plurality of orifices extending therethrough, a porous membrane). Passive droplet ejection devices could be used as well, or those which are "powered" solely by the inhalation of the individual using the portable inhaler. As such, virtually any type of inhaler may be utilized in relation to the present invention.

Power recharge capabilities may be provided by the present invention in addition to the flowable substance recharging capabilities noted above. The portable inhaler may include a first power supply and recharging contacts which are electrically interconnected therewith. These recharging contacts need not be in constant electrical communication with the first power supply, although such is preferred. The noted first power supply may be used to activate a droplet ejection device(s) which may be used by the portable inhaler to propel a flowable substance through one or more discharge orifices in some manner. Other components of the portable inhaler could be powered by the first power supply as well. An appropriate indicator of the power level of the first power supply of the portable inhaler may also be utilized by the portable inhaler for providing corresponding information to a user thereof. Any such power level indicator could provide an indication of the power remaining in the first power supply of the portable inhaler, or could simply be a two-state device which would simply indicate that there was either sufficient or insufficient power for proper operation of the inhaler.

Recharging of the first power supply for the portable inhaler may be provided by a power recharging system of the recharging unit. The noted power recharging system of the recharging unit may interface with the recharging unit's inhaler docking station and may include a second power supply and a power recharging fixture. The second power supply of the recharging unit may be rechargeable as well, such as by plugging the recharging unit into an appropriate electrical outlet. An appropriate indicator of the power level of the type noted for the first power supply of the portable inhaler may be used for the second power supply of the recharging unit as well. When the portable inhaler is disposed at the docking station of the recharging unit, the power recharging fixture of the recharging unit interfaces with the recharging contacts of the portable inhaler so as to allow the second power supply of the recharging unit to recharge the first power supply of the portable inhaler. Preferably, both the flowable substance and power for the portable inhaler are simultaneously recharged when the inhaler is docked at the recharging unit, although each could be done individually and/or independent of each other. Moreover, preferably the recharging unit includes an appropriate "recharging complete" indicator or the like.

The droplet ejection device which may be included in the portable inhaler may be electrically interconnected with the first power supply as noted above. This droplet ejection device may include a controller (e.g., printed circuit board) which may also be electrically interconnected with this first power supply. The portable inhaler may also include one or more electronic memories which may be powered by the first power supply as well, and further which may be characterized as actually being part of the noted controller. Activation of the droplet ejection device may be via a switch (e.g., manually by an individual activating the switch on the portable inhaler), or via an inhalation sensor (e.g., automatically via the inhalation sensor applying power to an appropriate circuit of a controller for the portable inhaler). Devices of this type may be electrically interconnected with the first power supply of the portable inhaler as well.

The docking station of the recharging unit may be in the form of a receptacle which at least generally approximates a contour of the portable inhaler housing when the portable inhaler is docked at the recharging unit. One appropriate configuration for the inhaler housing of the portable inhaler is cylindrical as noted above. In this case, the receptacle which defines the inhaler docking station may also then be in the form of a cylinder. Docking of the portable inhaler to the recharging unit may then entail directing the portable inhaler along an axial path relatively toward the recharging unit, while removal of the portable inhaler from the recharging unit may entail directing the portable inhaler relatively away from the recharging unit along an axial path, and thereby in the opposite direction from the docking operation. Features may be implemented to protect the portable inhaler when docked to the recharging unit (e.g., to protect from mechanical damage and/or contamination of some type), such as by enclosing the portable inhaler within the recharging through use of a sliding door or the like over the above-noted receptacle.

The recharging unit housing may be sized to a least generally approximate a package of cigarettes for purposes of portability and to account for the limited number of doses which may be made available in the portable inhaler. In one embodiment, the recharging unit occupies a space having a volume of no more than about 100 cc. The docking station of the recharging unit may also be configured so as to accept only a single portable inhaler (e.g., incorporating a lock out system to take only a specific inhaler), to reduce the potential for tampering with the recharging unit and the portable inhaler when docked thereto, and/or to reduce the potential for cross-filling between different portable inhalers. This may be used to prevent multiple portable inhalers from being recharged by the same recharging unit and/or to otherwise present misuse of the portable inhaler. Relatedly, access security componentry may be utilized in relation to the recharging unit and/or any portable inhaler associated therewith.

The flowable substance recharging reservoir of the recharging unit may be pressurized to provide for medicament rechargings, although a pump(s) or capillary action could also be utilized for transferring medicament to the portable inhaler when docked to the recharging unit. In the case of the pressure-based fluid transfer technique, this pressure may be isolated from the flowable substance recharging fixture by an appropriate valve or the like until recharging is desired. Having this valve in one position may isolate the flowable substance recharging reservoir from the associated flowable substance recharging fixture of the recharging unit, while having this valve in another position may allow flowable substance from the flowable substance recharging reservoir to flow to the flowable substance recharging fixture. Movement of this isolation valve of sorts between these two positions may be affected by docking the portable inhaler at the docking station of the recharging unit. For instance, a "snap-lock" mechanism may be used to dock the portable inhaler to the recharging unit, and to in turn to simultaneously establish/maintain fluid communication between the flowable substance recharging reservoir of the recharging unit and the flowable substance container of the portable inhaler. Removal of the portable inhaler from the docking station of the recharging unit in turn may automatically move any such valve back to its isolating position. This same type of valving arrangement could possibly be utilized if other fluid transfer techniques are utilized.

The flowable substance recharging fixture of the recharging unit may include a recharging needle. This recharging needle may penetrate the flowable substance container of the portable inhaler to establish fluid communication between the flowable substance recharging reservoir of the recharging unit and flowable substance container of the portable inhaler. Including a septum or the like may allow for this penetration during recharging and establishment of an appropriate sealing engagement between the recharging unit and the flowable substance container of the portable inhaler. However, including an absorbent pad for the flowable substance recharging fixture may be desirable to account for any small leakages which may occur.

The portable inhaler may include an electronic memory as noted, and which would typically be powered by the first power supply of the portable inhaler. Data on the use of the portable inhaler may be recorded to this electronic memory. Downloading of this data to one or more electronic memories associated with the recharging unit may be affected (e.g., automatically) when the portable inhaler is docked at the recharging unit. One or more appropriate data ports may be provided on the recharging unit to allow this data to in turn be downloaded to an external computer as well. One or more appropriate data ports could also be provided on the portable inhaler to allow information stored on any electronic memory associated therewith to be directly downloaded to an external computer as well. For cases when the portable inhaler includes a programmable controller or the like (e.g., for controlling a droplet ejection device), this external computer also may be used to transfer information to the recharging unit via an appropriate communications port, and then to the portable inhaler when docked to the recharging unit, to alter or change one or more parameters associated with the operating protocol of the portable inhaler. Relatedly, the recharging unit may be operatively interconnectable with a PDA (personal digital assistant), a cell phone, or the like to utilize the power and/or communication capabilities of the same. For instance, the recharging unit could be configured to establish communication with a remote monitoring station of some sort on any type of basis (e.g., periodically, when the portable inhaler was not removed from the recharging unit at a time for a required dosing) to transmit various types of information, either through the above-noted PDA or cell phone, or alternatively through communication capabilities which may be incorporated into the design of the recharging unit itself.

Further functionality may be incorporated into any electronic memory which is associated with the recharging unit. For instance, information regarding the insertion of the portable inhaler within the recharging unit (e.g., a docking operation) and extraction of the portable inhaler from the the recharging unit may be recorded on any such memory utilized by the recharging unit (e.g., an identification code associated with the subject portable inhaler so as to specifically identify the same where more than one portable inhaler may be used with the recharging unit, the time and date the subject portable inhaler was removed/extracted from the recharging unit, the time and date the subject portable inhaler was re-docked at the recharging unit). Other types of information may be recorded on any electronic memory utilized by the recharging unit, such as the amount of medicament and/or power remaining in the recharging unit for recharging the associated portable inhaler(s) associated therewith.

BRIEF DESCRIPTION OF THE, SEVERAL VIEWS OF THE DRAWING

FIG. 2 is a cutaway view of the portable inhaler of the respiratory delivery system of FIG. 1.

FIG. 3 is a side view of the embodiment of the portable inhaler of FIG. 2.

FIG. 4A is an end view of one embodiment of a droplet ejection device which may be used by the portable inhaler of FIG. 2.

FIG. 4B is a cross-sectional view of one of the droplet ejection assemblies of the droplet ejection device of FIG. 4A.

FIG. 7 is a cutaway, side view of a medicament recharging operation using the portable inhaler of FIG. 2 and the recharging unit of FIG. 5.

DETAILED DESCRIPTION OF THE INVENTION

Figure 1:
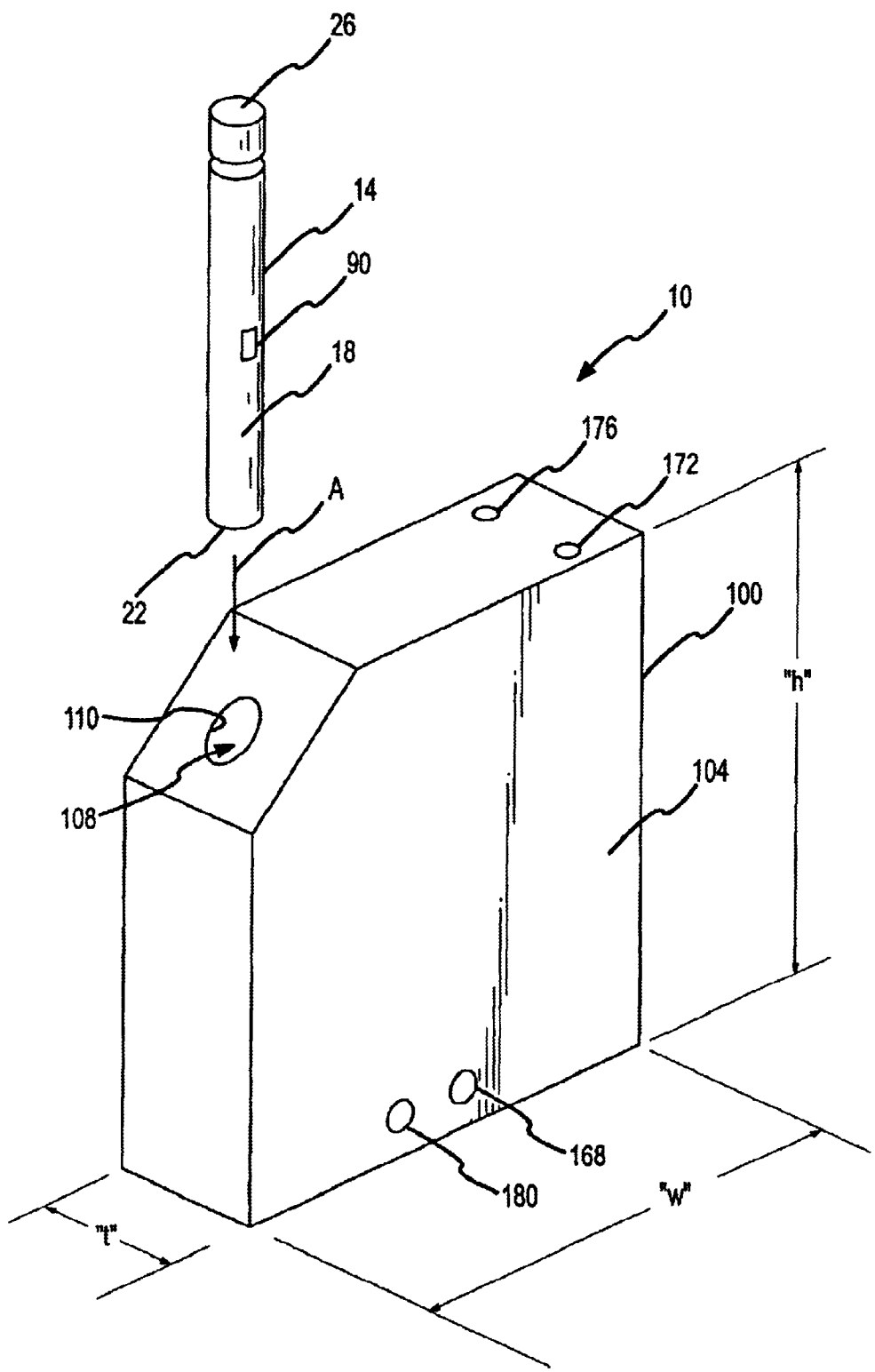
FIG. 1 is a perspective view of one embodiment of a respiratory delivery system.

The present invention will now be described in relation to the accompanying drawings which at least assist in illustrating its various pertinent features. One embodiment of a respiratory delivery system 10 is presented in FIG. 1. Basic components of the respiratory delivery system 10 include a portable inhaler 14 and a recharging unit 100. The inhaler 14 is portable and orally delivers any type of flowable substance to an individual. Most typically this will be some type of medicament which is stored in liquid form within the inhaler 14. Hereafter, the respiratory delivery system 10 will be described in relation to this medicinal application. However, gaseous substances could also be delivered by the inhaler 14, as well as non-medicinal substances both in liquid or gaseous form, as well as in powder form within a suspension. Moreover, the inhaler 14 could be used for topical or nasal delivery of these types of substances as well.

It may be desirable or required to limit the amount of medicament which may be stored within the portable inhaler 14. Moreover, certain designs for the portable inhaler 14 may require power. Recharges of both the medicament and power supplies of the portable inhaler 14 are provided by the respiratory delivery system 10 through its recharging unit 100. Other functions may be provided by the recharging unit 100 as well. For instance, data on the use of the portable inhaler 14 may be recorded by the inhaler 14 and downloaded/transferred to the recharging unit 100 when the inhaler 14 is docked thereto. The recharging unit 100 may also record data on usage of any portable inhaler 14 associated therewith. Further details on these and other features of the respiratory delivery system 10 and the two basic components thereof, namely the inhaler 14 and recharging unit 100, will now be addressed in more detail.

Two fundamental assemblies define the inhaler 14. One is a dispensing assembly 16 and the other is a cartridge assembly 28. Generally, the dispensing assembly 16 includes certain electronics for affecting the operation of the inhaler 14 and recording information on the use thereof. On the other hand, the cartridge assembly 28 includes a supply of medicament and a "head" of sorts through which medicament is discharged from the inhaler 14 in the form of droplets. Preferably, the cartridge assembly 28 is detachably interconnected with the dispensing assembly 16. That is, preferably the cartridge assembly 28 may be installed in/on the dispensing assembly 16 by the individual for a respiratory treatment, and thereafter removed from the dispensing assembly 16. This same individual may then install another cartridge assembly 28 in/on the dispensing assembly 16 at a later time for another respiratory treatment with a different medicament. More than one individual could use the same dispensing assembly 16 for affecting a respiratory treatment or the like as well. For instance, a family may have a single dispensing assembly 16, and each family member which is in need of respiratory therapy of some type may have their own cartridge assembly 28 or assemblies 28.

Details of one design for the portable inhaler 14 are presented in FIGS. 2–3. One component of the dispensing assembly 16 for the inhaler 14 is an at least generally cylindrical housing 18 which in one embodiment is configured/sized so as to least simulate or be representative of a conventional cigarette. In one embodiment, the housing 18 has a length within a range of about 50 mm to about 150 mm, and a diameter within a range of about 5 mm to about 30 mm. The size of the inhaler housing 18 is dependent on the required "life" of its onboard power supply 74 and/or the total volume of medicament contained in its onboard medicament container 46, both of which are addressed in more detail below. Although the illustrated embodiment is of cylindrical shape throughout the entire extent of the inhaler housing 18, a different shape could be implemented, such as in the region of the power supply 74 to provide a pipe-type shape (e.g., to accommodate a larger sized power supply 74 in the "bulbous" region of such a pipe-type shape).

Discharges from the inhaler 14 are through an end 22 of the housing 18 which defines a discharge outlet. Typically the discharge end 22 of the housing 18 is inserted within the mouth of an individual that is using the inhaler 14. A mouthpiece or the like could be formed on the discharge end 22 of the inhaler 14 if desired as well (not shown). Disposed opposite the discharge end 22 of the inhaler housing 18 is an end 26. Certain electrical components are preferably utilized by the inhaler 14. Airflow past these components could possibly have an adverse effect on their operation. Therefore, in one embodiment the end 26 of the inhaler housing 18 is closed. Air is instead drawn within the inhaler housing 18, for the introduction of a plurality of droplets therein for inhalation by an individual using the inhaler 14 in a manner which will be discussed in more detail below, through a plurality of air intakes slots 82 which extend through the inhaler housing 18 as shown in FIG. 3 and which each define an inhaler inlet. Generally the noted electrical components are located within the inhaler housing 18 somewhere between the air intake slots 82 and the closed end 26 of the inhaler housing 18 so that airflow is not directed thereby during inhalation by an individual using the inhaler 14. Other characteristics of these air intake slots 82 are that: 1) they have a longitudinal extent which is at least generally parallel with a longitudinal extent of the inhaler 14 and more specifically the inhaler housing 18; and 2) at least a substantially equal radial or arcuate spacing is utilized between adjacent air intake slots 82. Notwithstanding these potential benefits of the slots 82, one or more air intake orifices could be disposed on the end 26 of the inhaler housing 18 or at other appropriate locations on the inhaler housing 18.

The cartridge assembly 28 is detachably interconnected with the inhaler housing 18 of the dispensing assembly 16 such that one cartridge assembly 28 may be removed from the inhaler housing 18 by an individual and replaced with a structurally similar cartridge assembly 28. A "snap-lock" interconnection between the cartridge assembly 28 and inhaler housing 18 may be utilized (not shown). An appropriate button or other mechanism may be utilized to remove the cartridge assembly 28 from within the inhaler housing 18 or to disengage the "snap-lock" interconnection. Both insertion and removal of the cartridge assembly 28 may be through the discharge end 22 of the inhaler housing 18, although the inhaler housing 18 could be formed in multiple and detachably interconnected parts as well (e.g., through a threaded interconnection) to provide for installation and removal of the cartridge assembly 28 as well (not shown). In any case, one reason for providing a readily removable cartridge assembly 28 is to allow an individual to use the same inhaler 14 to discharge multiple medications. More than one individual could also use the same inhaler 14 to discharge one or more medications contained in one or more cartridge assemblies 28 possessed by a given individual. Further details regarding these types of features will be addressed in more detail below.

The cartridge assembly 28 includes a medicament container 46 which contains a supply of a certain medicament. Multiple medicament containers 46 could also be utilized by the cartridge assembly 28 to provide for the discharge of medicaments simultaneously or any one medicament dependent on need (not shown). Various types of information regarding this medicament and/or this particular medicament container 46 are stored electronically on a chip 48 which is attached to or integrally formed with the medicament container 46. Information which may be included on the chip 48 includes: 1) the identity of the particular medicament within the medicament container 46; 2) the type of this particular medicament; 3) the concentration of this particular medicament; 4) the total volume of this particular medicament initially included within the medicament container 46 before any discharges to an individual; 5) the identity of the individual designated for use of the medicament stored in the medicament container 46; 6) relevant limitations regarding the use of the medicament stored in the medicament container 46 (e.g., not to be used within a the certain time period of an administration of a different medicament which may be contained in another cartridge assembly 28 and discharged from the same inhaler 14, or so as to reduce the potential for having adverse medicament interactions from multiple dosings using the inhaler 14); 7) a protocol for controlling the discharge of the medicament from the medicament container 46 (e.g., an actuation signal, required time intervals between "dosing events", with each "dosing event" being a single or predetermined number of discharges from the inhaler 14); 8) an access code which must be entered in order for the inhaler 14 to be operational with the particular cartridge assembly 28; and 9)"protocol" regarding how dispensation of medicament and/or the amount thereof should be modified, if at all, based upon patient requirements or otherwise. Data on the use of the cartridge assembly 28 may also be recorded on the chip 48 in an appropriate database structure or the like (e.g., the chip 48 may also include one or more electronic memories). For instance, the time and date of each "dosing event" or each single discharge from the inhaler 14 may be recorded on the chip 48 for future use/evaluation. The portable inhaler 14 need not include data storage capabilities in all instances.

Only a limited amount of medicament may be stored in the container 46 of a given cartridge assembly 28, particularly in those instances where the inhaler 14 at least a simulates the size and appearance of a conventional cigarette. Assume that a dose is defined as the amount of medicament which is discharged from the inhaler 14 during a single inhalation by an individual that is using the inhaler 14. In one embodiment and in accordance with this definition of a "dose," the medicament container 46 may be sized so as to hold no more than about 50 of such "doses." Recharges of the supply of medicament for the medicament container 46 is desired since the cartridge assembly 28 also includes at least one droplet ejection device 30, and therefore may be too expensive for discarding after depleting the contents of the medicament container 46. More than one cartridge assembly 28 could also be utilized by the portable inhaler 14 as well which would further increase the need/desirability for rechargings. In any case, the subject medicament rechargings are facilitated by a septum 50 which is disposed on an end of the medicament container 46 which least generally projects toward the discharge end 22 of the inhaler housing 18 when the cartridge assembly 28 is installed to the dispensing assembly 16. In one embodiment, the septum 50 is formed from N-butyl rubber.

Medicament from the medicament container 46 is discharged from the portable inhaler 14 preferably in the form of a plurality droplets which are carried out through the discharge end 22 of the inhaler housing 18 by an inhalation stream. In this regard, each cartridge assembly 28 for the inhaler 14 also includes a droplet ejection device 30 as noted, which is fluidly interconnected with its corresponding medicament container 46 by an appropriate fluid interconnect 54. Any way of fluidly interconnecting the droplet ejection device 30 and medicament container 46 maybe utilized. The droplet ejection device 30 projects at least generally toward the discharge end 22 of the inhaler housing 18 when loaded within the inhaler 14. Typically, the droplet ejection device 30 will be disposed at a distance from the discharge end 22 of the inhaler housing 18 which is within a range of about 2 mm to about 30 mm.

Various types of delivery or ejection techniques/componentry may be utilized by the inhaler 14, including those presented in U.S. Pat. No. 5,894,841 to Voges, which issued Apr. 20, 1999, and which is incorporated by reference in its entirety herein. Details of one embodiment of the droplet ejection device 30 are presented in FIGS. 4A–B. The droplet ejection device 30 includes a plurality of droplet ejection assemblies 32. Each droplet ejection assembly 32 includes an actuator 42 which is aligned with and separated from a corresponding discharge orifice 34 by a space 38. Medicament from the medicament container 46 is disposed within this space 38 at least just prior to ejection (e.g., medicament may be continually within the space 38; all or substantially all of the medicament within the space 38 associated with the particular droplet ejection assembly 32 may be discharged on actuation thereof, and thereafter may be replenished after such an actuation). Actuation of the portable inhaler 14 causes each actuator 42 which receives an actuation signal to discharge medicament through its corresponding discharge orifice 34 in the form of one and typically a plurality of droplets. All of the actuators 42 may be activated simultaneously, or the plurality of actuators 42 may be activated in some type of sequence or firing pattern.

In one embodiment, the actuators 42 are resistors and the actuation signal provided thereto affects a rapid increase in the temperature of an actuator 42 which receives such a signal. This rapid increase in the temperature of each "activated" actuator 42 forms/creates a bubble directly adjacent to the actuator 42. Enlargement of this bubble in the direction of its corresponding discharge orifice 34 from the rapid temperature increase displaces that medicament, which is located between the bubble and the corresponding discharge orifice 34, out through the discharge orifice 34.

Activation of any droplet ejection assembly 32 of the droplet ejection device 30 may be affected through a controller assembly 62 which is part of the dispensing assembly 16 of the inhaler 14. In this regard, an appropriate operative interconnect 70 extends between and interconnects the droplet ejection device 30 and the controller assembly 62, while another operative interconnect 72 extends between and interconnects the chip 48 of the medicament container 46 and the controller assembly 62. Any way of appropriately operatively interconnecting the controller assembly 62 of the dispensing assembly 16 and the cartridge assembly 28 may be utilized. In fact, the "electronics" or one or more aspects of the control assembly 62 could actually be incorporated into the structure of the droplet ejection device 30. In any case, the controller assembly 62 may include one or more of a microprocessor, a programmable logic control, an electronic memory or memories, and one or more clocks. Generally, the controller assembly 62 is able to read an operating protocol which is stored on the chip 48 of the cartridge assembly 28 and to operate the droplet ejection device 30 of the cartridge assembly 28 in accordance with this protocol (e.g., the number of discharges which define a "dosing event," the lapse of time required between individual discharges, the lapse of time required between dosing events). Various types of data may also be preferably stored on/through the controller assembly 62. For instance, the time and date of each actuation of the inhaler 14 may be recorded/ retained for future use/evaluation. Moreover, information for controlling access (e.g., security) to or in relation to the portable inhaler 14 may be stored on/through the controller assembly 62, as may be information relating to controlling the operation of the inhaler 14.

Components of the controller assembly 62 are powered by an "on-board" power supply 74 (e.g., rechargeable battery) which is operatively/electrically interconnected therewith, and which is also part of the dispensing assembly 16. Other components of the inhaler 14 may be electrically interconnected with the power supply 74 as well. Activation of the inhaler 14 may be automated via an appropriate sensor 58 (e.g., airflow, pressure) which is operatively interconnected with the controller assembly 62, and thereby the power supply 74, through the controller assembly 62. The sensor 58 is also part of the dispensing assembly 16. Detection of a certain airflow within the inhaler housing 18 may cause the sensor 58 to send a signal to the controller assembly 62, which in turn may send an actuation signal (e.g., a single pulse or a series of defined pulses) over the operative interconnect 70 to the droplet ejection device 30. Droplets of medicament may then be discharged from the droplet ejection device 30 in the above-noted manner. Manual operation of the inhaler 14 may be provided by including an activation switch 86 of the dispensing assembly 16 on an exterior portion of the inhaler housing 18 and which would be operatively interconnected with the controller assembly 62, and thereby the power supply 74. Activating the switch 86 would then send a signal to the controller assembly 62, which in turn would send an actuation signal (e.g., a single pulse or a series of defined pulses) over the operative interconnect 70 to the droplet ejection device 30. Droplets of flowable substance may then be discharged from the droplet ejection device 30 in the above-noted manner. One or both, sensor 58 and activation switch 86 may be used in the design of the inhaler 14.

Depletion of the energy within the power supply 74 may adversely affect or preclude the operation of the portable inhaler 14. Existing energy levels within the power supply 74 may be monitored through some type of a power indicator 90 of the dispensing assembly 16 (FIG. 1). One implementation of the power indicator 90 would simply be to provide one type of indication when sufficient power existed within the power supply 74 (e.g., a "light on" or "light off" condition) and to provide another type of indication when insufficient power existed within the power supply 74 (e.g., the converse). Another option would be to somehow actually display the current power level of-the power supply 74. In any case, the power supply 74 will only be able to operate the inhaler 14 for a fixed amount of time. Therefore, the inhaler 14 further includes a pair of inhaler recharging contacts 78 which are also part of the dispensing assembly 16. These recharging contacts 78 are exposed in at least some manner on the exterior of the inhaler housing 18 and are electrically interconnectable or interconnected with the power supply 74 (e.g., the contacts 78 need not be continuously electrically interconnected with the power supply 74).

Figure 5:
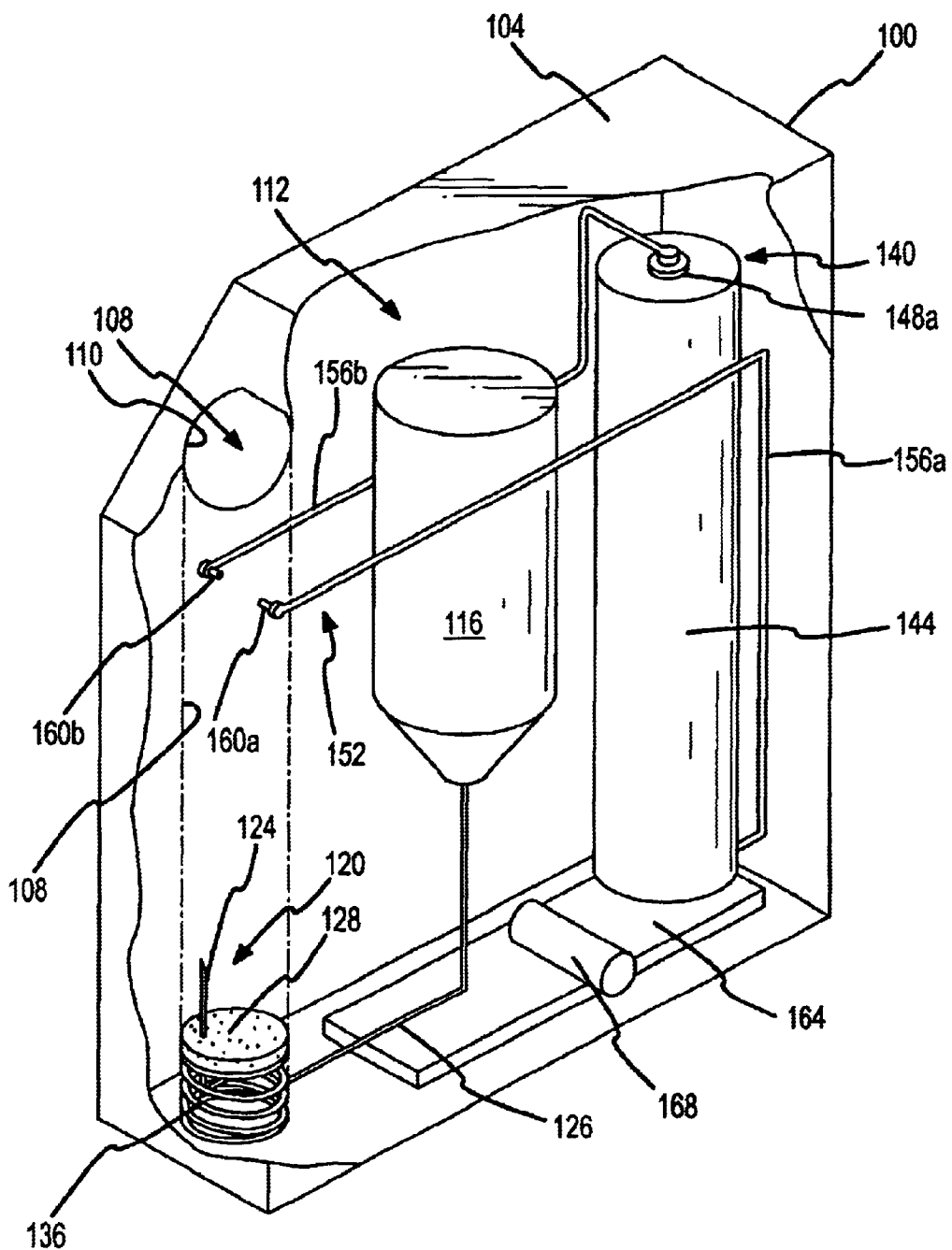
FIG. 5 is a cutaway, perspective view of the recharging unit of the respiratory delivery system of FIG. 1.
Figure 6:
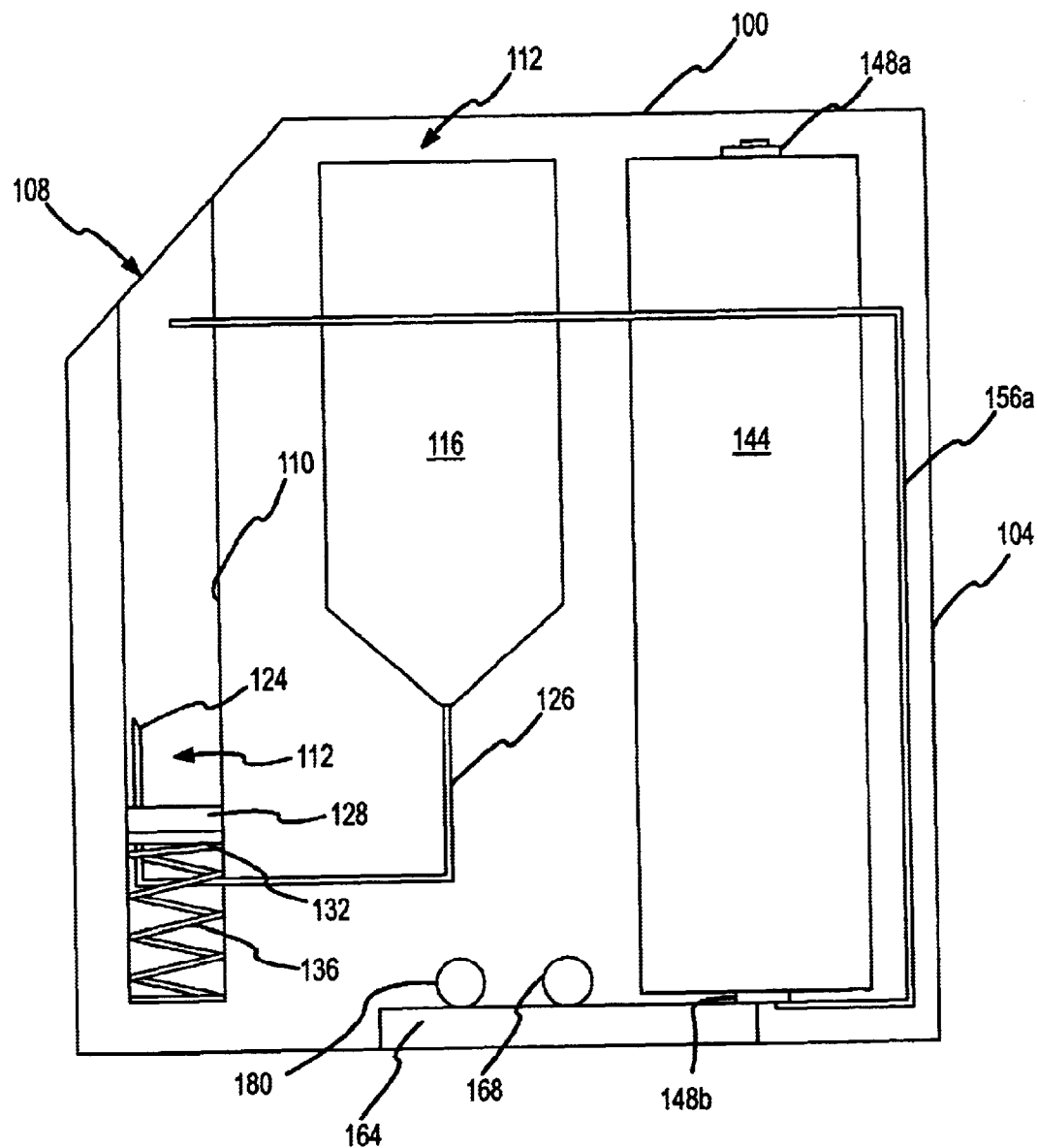
FIG. 6 is a cutaway, side view of the recharging unit presented in FIG. 5.

Recharges of medicament for the medicament container 46 of the portable inhaler 14 and energy for the power supply 74 of the inhaler 14 are provided through the recharging unit 100 of the respiratory delivery system 10. Details for one embodiment of the recharging unit 100 are presented in FIGS. 5–6. The recharging unit 100 generally includes a recharging unit housing 104 which in one embodiment is configured/sized at least generally in the manner of the conventional package of cigarettes. In one embodiment, the recharging unit 100 has a height "h" which is within a range of about 100 mm to about 150 mm, a width "w" which is within a range of about 40 mm to about 80 mm, and a thickness "t" which is within a range of about 15 mm to about 40 mm. Another way of characterizing the size of recharging unit housing 104 is through the volume of space which it occupies. In one embodiment, the volume of space which is occupied by the recharging unit housing 104 is within a range of about 60 cc to about 480 cc.

Appropriate interconnection between the portable inhaler 14 and recharging unit 100 is affected by including an inhaler docking station 108 within the recharging unit housing 104. Generally, the inhaler docking station 108 includes an elongated aperture or recess 110 which is sized/ configured to least generally approximate the perimeter of the housing 18 of the inhaler 14. In one embodiment, the docking station recess 110 is at least generally cylindrical with a diameter which is about 11 mm. The height of the inhaler docking station recess 110 in one embodiment is selected such that at least part of the inhaler housing 18 extends beyond the recharging unit housing 104 When the inhaler 14 is completely docked to the recharging unit 100 (e.g., fully seated therewithin and preferably "locked" relative thereto). However, the inhaler housing 18 could be disposed entirely within the recharging unit 100. In this case an appropriate "cover" could be utilized to reduce the potential for contamination by totally enclosing the portable inhaler 14 within the recharging unit 100 when docked thereto.

Recharging of the medicament container 46 of the inhaler 14 when docked at the station 108 of the recharging unit 100 is provided by a medicament recharging system 112 of the recharging unit 100. The recharging unit 100 may be configured to "read" the chip 48 on the medicament container 46 of the inhaler 14 before being completely docked to the recharging unit 100 to verify that the medicament container 46 contains the same type of medicament as is in the medicament recharging reservoir 116 of the recharging unit 100. If such was not the case, the inhaler 14 could be precluded from being docked to the recharging unit 100 in a manner to affect a medicament recharging operation. Multiple medicaments could be stored within the recharging unit 100 in different reservoirs 116 (not shown), such that the above-noted "reading" of the chip 48 could be used to fluidly interconnect the inhaler 14 with the correct medicament recharging reservoir 116 within the recharging unit 100 (i.e., so as to fluidly interconnect "matching" medicaments).

Components of the medicament recharging system 112 include a medicament recharging reservoir 116, a medicament recharging fixture assembly 120, and an interconnecting medicament recharging conduit 126. Assume again that a dose is defined as the amount of medicament which is discharged from the inhaler 14 during a single inhalation by an individual that is using the inhaler 14. In one embodiment and in accordance with this definition of a "dose," the medicament recharging reservoir 116 may be sized so as to hold within a range of about 150 of such "doses" to about 3,000 of such "doses." Preferably the medicament recharging system 112 is pressurized for injecting the medicament into the medicament container 46 when the inhaler 14 is docked at the station 108 of the recharging unit 100. Other types of pumping and/or capillary action could be utilized to affect fluid transfer. The supply of medicament for the medicament recharging reservoir 116 may be replenished through appropriate structure (not shown, but via a fitting which is fluidly interconnected with the medicament recharging reservoir 116 and which is exposed on exterior surface of the recharging unit housing 104).

The medicament recharging fixture assembly 120 is disposed within the lower portion of the docking station recess 110 and interfaces with the inhaler 114 through its discharge end 22 when docked at the station 108. Components of the medicament recharging fixture assembly 120 include an appropriate mount 132 which is slidably mounted within the docking station recess 110 via a spring 136 or other appropriate mechanism which exerts a biasing force which is directed opposite to the direction in which the inhaler 14 moves relative to the recharging unit 100 when being docked thereto, an absorbent pad 128 which is disposed on this mount 132, and a medicament recharging needle 124 which is fluidly interconnected with the medicament recharging conduit 126 and which extends through both the mount 132 and the absorbent pad 128 to establish an appropriate interface with the medicament container 46. More specifically and referring now to both FIGS. 1 and 7, when the portable inhaler 14 is moved along an axial path in the direction of the arrow A (FIG. 1) so as to direct the inhaler 14 downwardly within the docking station recess 110, the medicament recharging needle 124 will engage the septum 50 on the medicament container 46. Various techniques may be employed to ensure that the inhaler 14 is disposed within the proper position relative to the recharging unit 100 when being directed within the docking station recess 110 so as to realize this engagement (not shown).

Initial engagement of the medicament recharging needle 124 against the septum 50 will typically cause the spring 136 to compress or move in the direction of the arrow A in FIG. 1. At a certain point in time of this compression of the biasing spring 136, the medicament recharging needle 124 will penetrate and thereafter pass entirely through the septum 50 so as to fluidly interconnect the medicament recharging reservoir 116 with the medicament container 46. Typically the inhaler 14 will then be "locked" into a fixed position relative to the recharging unit 100, such as by a snap-lock interconnection or the like (not shown). Medicament will then flow from the medicament recharging reservoir 116, through the medicament recharging conduit 126 and medicament recharging needle 124, and into the medicament container 46. Recharging of the medicament container 46 of the inhaler 14 may be complete when the pressure within the medicament recharging reservoir 116 is equal to the pressure within the medicament container 46.

Existing medicament levels or amounts within the medicament recharging reservoir 116 may be monitored through some type of a medicament indicator 176 on or associated with recharging unit 100. One implementation of the medicament indicator 176 would simply be to provide one type of indication when sufficient medicament existed within the medicament recharging reservoir 116 for recharging an appropriate cartridge assembly 28 (e.g., a "light on" or "light off" condition) and to provide another type of indication when insufficient medicament existed within the medicament recharging reservoir 116 to affect a recharging (e.g., the converse). Another option would be to somehow display the actual level or amount of medicament remaining in the medicament recharging reservoir 116 and available for recharging an appropriate cartridge assembly 28.

Power recharge operations are also affected when the inhaler 14 is docked at the station 108 of the recharging unit 100. Preferably power recharging operations and medicament recharging operations are affected simultaneously. Recharging of the power supply 74 of the inhaler 14 is provided by a power recharging system 140 of the recharging unit 100. Components of the power recharging system 140 include a power supply 144 having a pair of oppositely charged terminals 148a–b and a pair of electrical leads 156a–b. Each electrical lead 156a–b extends from the corresponding terminal 148a–b of the power supply 144. Appropriate contacts 160a–b are disposed on the ends of the corresponding electrical leads 156a–b and are located at least proximate to, and preferably at least partially within, the docking station recess 110 at the appropriate elevation therewithin (e.g., so as to appropriately interface with the inhaler recharging contacts 78 when the inhaler 14 is completely docked to the recharging unit 100). In one embodiment, the pair of electrical leads 156a–b and their corresponding contacts 160a–b are biased towards each other. Advancement of the inhaler 14 downwardly within the docking station recess 110 may initially move the pair of contacts 160a–b away from each other and against this biasing force. Appropriate structure may be incorporated proximate the discharge end 22 of the inhaler housing 18 to facilitate the initial engagement between inhaler housing 18 and the contacts 160a–b of the power recharging system 140. In any case, when the inhaler 14 is completely docked to the recharging unit 100 (e.g., positionally "locked"), the contacts 160a–b of the power recharging system 140 will be in appropriate electrical contact with the recharging contacts 78 on the inhaler 14. In cases where the inhaler recharging contacts 78 are recessed to a degree relative to the exterior surface of the inhaler housing 18, the biasing forces which are incorporated into the leads 156a–b of the power recharging system 140 will direct its contacts 160a–b toward and into appropriate engagement with their corresponding recharging contact 78 on the inhaler 14. Energy from the power supply 144 of the recharging unit 100 may then be directed to the power supply 74 of the inhaler 14 to recharge the same.

Depletion of the power available in the power supply 144 of the recharging unit 100 for recharging the power supply 74 of the portable inhaler 14 may be addressed through use of a recharge connector 168 of the recharging unit 100 which is operatively interconnected with the power supply 144. An appropriate cord, cable, or the like may be inserted into the recharge connector 168 and plugged into a conventional wall outlet to recharge the power supply 144 of the recharging unit 100. Existing energy levels within the power supply 144 may be monitored through some type of a power indicator 172 which is on or otherwise associated with the recharging unit housing 104. One implementation of the power indicator 172 would simply be to provide one type of indication when sufficient power existed within the power supply 144 for affecting a recharging operation (e.g., a "light on" or "light off" condition) and to provide another type of indication when insufficient power existed within the power supply 144 for affecting a recharging operation (e.g., the converse). Another option would be to somehow display the actual power level of the power supply 144 which is available for affecting recharging operations.

Further functions may be provided by the respiratory delivery system 10 when the inhaler 14 is appropriately docked to the recharging unit 100. For instance, data from the controller assembly 62 of the inhaler 14 may be downloaded onto a controller 164 of the recharging unit 100 which includes one or more electronic memories. Data transfer operations may be automatically affected when the inhaler 14 is docked at the recharging unit 100. This data in turn may be downloaded to an external computer (not shown) through a data transfer port 180.

There are a number of "management" implementations which may be utilized in relation to the respiratory delivery system 10 based upon the combination of components thereof as described above. For instance, the inhaler 14 may include an appropriate data entry device of some type or other means (not shown) for inputting an access to code for "activating" the inhaler 14 (e.g., for allowing discharges from a cartridge assembly 28 which is appropriately loaded within the dispensing assembly 16). This access code may be specific to a certain cartridge assembly 28 and may be stored on its corresponding chip 48. When an individual loads a particular cartridge assembly 28 into the dispensing assembly 16, the individual may be required to somehow enter an appropriate access code before the controller assembly 62 of the dispensing assembly 16 for the inhaler 14 will allow medicament to be discharged from the cartridge assembly 28.

The same dispensing assembly 16 again may be used with multiple cartridge assemblies 28 of an appropriate configuration. One cartridge assembly 28 may be loaded within the dispensing assembly 16 to discharge one type of medicament, while another cartridge assembly 28 may be loaded within the dispensing assembly 16 to discharge another type of medicament. Similarly, one cartridge assembly 28 which is "assigned" to a certain individual may be loaded within the dispensing assembly 16 for discharge of its corresponding medicament, while another cartridge assembly which is "assigned" to a different individual may be loaded within the dispensing assembly 16 for discharge of its corresponding medicament. These medicaments in the latter example may be of the same type or of a different type. In any case, appropriate data may be stored on/through the controller assembly 62 of the dispensing assembly 16 for the inhaler 14 which identifies each cartridge assembly 28 which has been loaded within the dispensing assembly 16, the time and date when a particular cartridge assembly 28 was loaded within the dispensing assembly 16, and/or the time and date when such a cartridge assembly 28 was thereafter removed from the dispensing assembly 16. Data on each "firing" of any cartridge assembly 28 loaded within the inhaler 14 may be recorded on the controller assembly 62 as well (e.g., each discharge from the inhaler 14). This data may then be downloaded to the recharging unit 100 for storage on its controller 164 when the inhaler 14 is appropriately docked at the recharging unit 100. Alternatively, the data may be downloaded from the controller assembly 62 of the inhaler 14 to an external device which is operatively interconnected with the recharging unit 100 through its data transfer port 180 and when the inhaler 14 is appropriately docked to the recharging unit 100 (e.g., the recharging unit 100 would simply be a "pass through" device in this instance).

The foregoing description of the present invention has been presented for purposes of illustration and description. Furthermore, the description is not intended to limit the invention to the form disclosed herein. For instance, although the delivery system 2 has been described with regard to respiratory delivery, topical deliveries could be affected as well with the system 2. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A respiratory delivery system, comprising:

a portable inhaler which comprises an inhaler housing, a first medicament container associated with said inhaler housing, and a first discharge outlet which is at least fluidly interconnectable with said first medicament container and through which a discharge from said portable inhaler is directed to a mouth of a user of said portable inhaler; and a recharging unit which comprises an inhaler docking station and a medicament recharging system which interfaces with said docking station, wherein said medicament recharging system comprises a medicament recharging reservoir and a medicament recharging fixture which interfaces with said first medicament container of said portable inhaler when said portable inhaler is disposed at said docking station of said recharging unit and through which a medicament from said medicament recharging reservoir flows to said first medicament container.

2. A system, as claimed in claim 1, wherein:

said inhaler housing approximates a configuration of a cigarette.

3. A system, as claimed in claim 1, wherein:

said inhaler housing comprises at least one inhaler inlet.

4. A system, as claimed in claim 3, wherein:

said at least one inhaler inlet is disposed on a sidewall of said inhaler housing.

5. A system, as claimed in claim 3, wherein:

said inhaler housing comprises first and second ends, wherein said first discharge outlet is disposed at said second end, and wherein said at least one inhaler inlet is disposed on said first end.

6. A system, as claimed in claim 3, wherein:

said at least one inhaler inlet comprises a plurality of air intake slots each having a longitudinal extent which is at least generally parallel with a longitudinal extent of said inhaler housing.

7. A system, as claimed in claim 1, wherein:

said first medicament container is sized to hold no more than about 50 doses of a medicament, wherein one dose of said no more than about 50 doses is discharged from said portable inhaler on each inhalation by said user.

8. A system, as claimed in claim 7, wherein:

said medicament recharging reservoir is sized to hold an amount of medicament which is within a range of about 150 to about 3,000 doses of said medicament.

9. A system, as claimed in claim 1, wherein:

a medicament disposed in said first medicament container is a liquid.

10. A system, as claimed in claim 1 wherein:

said inhaler housing comprises first and second ends, wherein said first discharge outlet is disposed at said second end, and wherein said first medicament container is disposed closer to said second end than said first end.

11. A system, as claimed in claim 1, wherein:

said portable inhaler further comprises a droplet ejection device which is fluidly interconnected with said first medicament container, wherein said droplet ejection device and said first medicament container define a cartridge assembly which is detachably interconnected with said inhaler housing.

12. A system, as claimed in claim 1, wherein:

said portable inhaler further comprises a first power supply and recharging contacts electrically interconnected with said first power supply, wherein said recharging unit further comprises a power recharging system which interfaces with said inhaler docking station, and wherein said power recharging system comprises a second power supply and a power recharging fixture which interfaces with said recharging contacts of said portable inhaler when said portable inhaler is disposed at said docking station of said recharging unit and through which energy from said second power supply of said recharging unit is directed to said first power supply of said portable inhaler.

13. A system, as claimed in claim 12, wherein:

said portable inhaler further comprises a droplet ejection device which is electrically interconnected with said first power supply and fluidly interconnected with said first medicament container.

14. A system, as claimed in claim 13, wherein:

said inhaler further comprises a controller which is electrically interconnected with said first power supply and operatively interconnected with said droplet ejection device.

15. A system, as claimed in claim 14, wherein:

said controller comprises a printed circuit board.

16. A system, as claimed in claim 13, wherein:

said portable inhaler further comprises an activation switch on an exterior of said inhaler housing which is electrically interconnected with both said first power supply and said droplet ejection device.

17. A system, as claimed in claim 13, wherein:

said portable inhaler further comprises an airflow sensor which is electrically interconnected with both said first power supply and said droplet ejection device.

18. A system, as claimed in claim 12, wherein:

said a first and second power supplies each comprise a battery.

19. A system, as claimed in claim 12, wherein:

said power recharging system of said recharging unit further comprises means for recharging said second power supply.

20. A system, as claimed in claim 12, wherein:

said recharging unit comprises first and second indicators, wherein said first indicator is associated with an amount of medicament remaining in said recharging medicament reservoir and said second indicator is associated with an amount of power remaining in said second power supply.

21. A system, as claimed in claim 1, wherein:

said docking station of said recharging unit comprises a receptacle which at least generally approximates a contour of said inhaler housing when disposed at said docking station of said recharging unit.

22. A system, as claimed in claim 1, wherein:

said recharging unit is sized to approximate a package of cigarettes.

23. A system, as claimed in claim 1, wherein:

said docking station comprises an at least generally cylindrical aperture formed in a housing of said recharging unit.

24. A system, as claimed in claim 1, wherein:

said medicament recharging reservoir comprises means for affecting a flow of medicament.

25. A system, as claimed in claim 1, wherein:

said medicament recharging fixture comprises a medicament recharging valve movable between first and second positions, wherein said valve is in said first position when said portable inhaler is out of said docking station and precludes flow from said medicament recharging reservoir through said medicament recharging fixture, and wherein said valve is in said second position when said portable inhaler is in said docking station and allows flow from said medicament recharging reservoir through said medicament recharging fixture.

26. A system, as claimed in claim 1, wherein:

said medicament recharging fixture comprises a medicament recharging needle.

27. A system, as claimed in claim 26, wherein:

said first medicament container of said portable inhaler comprises a septum which sealingly interfaces with said medicament recharging needle when extending through said septum.

28. A system, as claimed in claim 1, wherein:

said medicament recharging fixture comprises an absorbent pad which interfaces with an end of said inhaler housing through which medicament from said medicament recharging reservoir is directed to said first medicament container of said portable inhaler.

29. A system, as claimed in claim 1, wherein:

said recharging unit comprises a "recharge complete" indicator.

30. A method for dispensing a liquid from a portable inhaler, comprising the steps of:

disposing said portable inhaler at a docking station of a recharging unit;

directing a liquid stored by said recharging unit into a container of said portable inhaler after said disposing step;

removing said portable inhaler from said docking station of said recharging unit; and dispensing at least a portion of said liquid from said container of said portable inhaler into a mouth of an individual.

31. A method, as claimed in claim 30, wherein:

said disposing step comprises directing said portable inhaler into an at least generally cylindrical aperture formed in a housing of said recharging unit.

32. A method, as claimed in claim 30, wherein:

said disposing step comprises requiring said portable inhaler to be disposed in a predetermined position relative to said docking station for execution of said disposing step.

33. A method, as claimed in claim 30, wherein:

said disposing step comprises moving said portable inhaler relative to said recharging unit along an at least a substantially axial path.

34. A method, as claimed in claim 30, wherein:

said directing step comprises storing a supply of said liquid under pressure in said recharging unit.

35. A method, as claimed in claim 30, wherein:

said directing step comprises in disposing a fill device through an end of said portable inhaler through which said dispensing step is executed.

36. A method, as claimed in claim 30, wherein:

said directing step comprises disposing an absorbent material against a portion of said container through which said directing step is executed.

37. A method, as claimed in claim 30, wherein:

said removing step comprises moving said portable inhaler relative to said recharging unit along an at least a substantially axial path.

38. A method, as claimed in claim 30, wherein:

said removing step comprises moving said portable inhaler away from said recharging unit in a first direction, and wherein said disposing step comprises moving said portable inhaler toward said recharging unit in a second direction which is directly opposite said first direction.

39. A method, as claimed in claim 30, wherein:

said dispensing step comprises dispensing droplets of said at least a portion of said liquid.

40. A method, as claimed in claim 30, further comprising the steps of:

repeating said dispensing step no more than about ten times; and requiring repetition of said disposing, directing, and said removing steps before any further execution of said dispensing step after said repeating step.

41. A method, as claimed in claim 30, further comprising the step of:

storing said recharging unit on said individual.

42. A method, as claimed in claim 30, further comprising the step(s) of:

recharging a power supply of said portable inhaler after said disposing step and before said removing step, wherein said recharging step uses a recharging unit power supply.

43. A method, as claimed in claim 42, further comprising the step of:

recharging said recharging unit power supply.

44. A method, as claimed in claim 42, wherein:

said recharging and directing steps are executed simultaneously.

45. A method, as claimed in claim 30, further comprising the step of:

configuring said recharging unit to be usable only by said portable inhaler.

46. A method, as claimed in claim 30, further comprising the steps of:

recording data on use each of said portable inhaler; and transferring said data from said portable inhaler to said recharging unit after said disposing step and before said removing step.

47. A method, as claimed in claim 46, further comprising the step of:

transferring said data from said recharging unit to a computer.

\* \* \* \* \*

UNITED STATES PATENT AND TRADEMARK OFFICE
CERTIFICATE OF CORRECTION

PATENT NO.    : 6,637,430 B1
DATED         : October 28, 2003
INVENTOR(S)   : Voges et al.

It is certified that error appears in the above-identified patent and that said Letters Patent is hereby corrected as shown below:

<u>Title page,</u>
Item [57], ABSTRACT,
Line 2, delete the word "plower", and insert therefor -- power --.

<u>Column 1,</u>
Line 46, delete the word "to,the", and insert therefore -- to the --.

Signed and Sealed this

Ninth Day of March, 2004

JON W. DUDAS
*Acting Director of the United States Patent and Trademark Office*